(12) United States Patent
Mukai et al.

(10) Patent No.: US 9,456,933 B2
(45) Date of Patent: Oct. 4, 2016

(54) DISPOSABLE WEARING ARTICLE

(75) Inventors: Hirotomo Mukai, Kagawa (JP); Takaya Arayama, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 470 days.

(21) Appl. No.: 14/130,353

(22) PCT Filed: Jun. 27, 2012

(86) PCT No.: PCT/JP2012/004168
§ 371 (c)(1),
(2), (4) Date: Mar. 12, 2014

(87) PCT Pub. No.: WO2013/005397
PCT Pub. Date: Jan. 10, 2013

(65) Prior Publication Data
US 2014/0188066 A1    Jul. 3, 2014

(30) Foreign Application Priority Data

Jul. 1, 2011  (JP) ................................ 2011-147784

(51) Int. Cl.
*A61F 13/15* (2006.01)
*A61F 13/49* (2006.01)
(Continued)

(52) U.S. Cl.
CPC ... *A61F 13/49007* (2013.01); *A61F 13/49001* (2013.01); *A61F 13/496* (2013.01);
(Continued)

(58) Field of Classification Search
CPC ...... A61F 13/45; A61F 13/53; A61F 13/532; A61F 13/5323; A61F 13/533; A61F 13/534; A61F 13/53409; A61F 13/53418; A61F 13/53427; A61F 2013/530437; A61F 2013/530445; A61F 2013/53454; A61F 2013/4512; A61F 2013/4518; A61F 2013/455; A61F 2013/4556; A61F 2013/4568; A61F 2013/4581
USPC ............ 604/378, 379, 380, 385.01, 385.201, 604/385.101
See application file for complete search history.

(56) References Cited

U.S. PATENT DOCUMENTS

2008/0140042 A1    6/2008  Mukai et al.

FOREIGN PATENT DOCUMENTS

EP    2520262 A1    11/2012
JP    3616077 B2     2/2005
(Continued)

OTHER PUBLICATIONS

Office Action mailed Jul. 28, 2015, corresponding to Japanese patent application No. 2011-147784.
(Continued)

*Primary Examiner* — Jacqueline Stephens
(74) *Attorney, Agent, or Firm* — Hauptman Ham, LLP

(57) ABSTRACT

A disposable wearing article includes an absorber having a crotch region. The central curving unit that allows the absorber to be convex in the inner direction is formed at a center in the widthwise direction of the crotch region. The first curving unit that allows the absorber to be convex in the outer direction is formed in the crotch region and outboard of the central curving unit. The second curving unit that allows the absorber to be convex in the inner direction is formed in the crotch region and outboard of the first curving unit. The concave unit is formed in the absorber to be concaved inwardly in the widthwise direction at the outside in the longitudinal direction relative to the first curving unit. The second curving unit is arranged outboard of an inside edge in the widthwise direction of the concave unit in the widthwise direction.

7 Claims, 11 Drawing Sheets

(51) Int. Cl.
*A61F 13/494* (2006.01)
*A61F 13/496* (2006.01)
*A61F 13/535* (2006.01)
*A61F 13/53* (2006.01)
*A61F 13/532* (2006.01)
*A61F 13/534* (2006.01)
*A61F 13/45* (2006.01)
*A61F 13/537* (2006.01)

(52) U.S. Cl.
CPC ....... *A61F13/49406* (2013.01); *A61F 13/534* (2013.01); *A61F 13/535* (2013.01); *A61F 13/45* (2013.01); *A61F 13/532* (2013.01); *A61F 13/5323* (2013.01); *A61F 13/53409* (2013.01); *A61F 13/53418* (2013.01); *A61F 2013/455* (2013.01); *A61F 2013/4512* (2013.01); *A61F 2013/49493* (2013.01); *A61F 2013/530437* (2013.01); *A61F 2013/530445* (2013.01); *A61F 2013/53454* (2013.01); *A61F 2013/53778* (2013.01); *A61F 2013/53786* (2013.01)

(56) References Cited

FOREIGN PATENT DOCUMENTS

| | | | |
|---|---|---|---|
| JP | 2006-346439 A | 12/2006 | |
| JP | 4092319 B2 | 5/2008 | |
| JP | 2011-031076 A | 2/2011 | |
| JP | 2012005538 | * 12/2012 | ............ A61F 13/15 |
| TW | 200913970 A | 4/2009 | |
| WO | 2008/069279 A1 | 6/2008 | |
| WO | 2012/108206 A1 | 8/2012 | |

OTHER PUBLICATIONS

Extended European Search Report issued Feb. 19, 2015, corresponding to European patent application No. 12807808.6.
Office Action in TW Application No. 101123266, mailed Nov. 23, 2015.
International Search Report issued in International Application No. PCT/JP2012/004168 on Sep. 18, 2012.

* cited by examiner

DISPOSABLE WEARING ARTICLE

RELATED APPLICATIONS

The present application is a U.S. National Phase entry of International Application No. PCT/JP2012/004168, filed Jun. 27, 2012, which claims priority from JP Application No. 2011-147784, filed Jul. 1, 2011.

TECHNICAL FIELD

The present disclosure relates to a disposable wearing article including a curving unit which is capable of curving an absorber.

BACKGROUND ART

In a disposable wearing article, such as a pants-type diaper, to improve the comfort of the wearer when worn and to prevent the leakage of excretions, various methods have been devised. For example, a disposable wearing article in which a curving unit capable of curving an absorber to a wearer's side is formed at the absorber is known. For example, Japanese Patent No. 4092319 describes a disposable wearing article in which a groove unit is formed along a front-back direction of an absorber that absorbs the excretions of a wearer.

In this disposable wearing article, three groove units as curving units are formed at the absorber, and when worn, the peripheral portion of each groove unit curves. A peripheral portion of a central groove unit is formed in a convex shape toward an excretion portion of a wearer. A peripheral portion of an intermediate groove unit which is positioned outboard of the central groove unit in the widthwise direction is formed in a concave shape relative to the excretion portion.

That is, in the absorber, a convex-shaped portion and a concave-shaped portion are formed alternatively adjacent to each other along the widthwise direction. Because the central portion of the absorber is in contact with the crotch portion of the wearer, the absorption performance can be improved. Furthermore, because the absorber curves along the crotch portion due to a plurality of curving units, the fitting improves.

CITATION LIST

Patent Literature

[PTL1] Japanese Patent No. 4092319 (FIG. 2 and FIG. 3)

SUMMARY OF INVENTION

However, the inventor(s) has/have recognized that, in the above-described disposable wearing article, curving units, which causes the absorber to be deformed in a convex shape, are also provided at a back waistline region arranged posteriorly of the crotch region and a front waistline arranged anteriorly of the crotch region as well as the crotch region that is adapted to be in contact with a crotch of the wearer. For example, the back waistline region that is arranged posteriorly of the crotch region is adapted to be in contact with the buttocks part of the wearer. If the concave-shaped portion and the convex-shaped portion are formed in this back waistline region, the absorber is not arranged along a bodyline, and there is an apprehension that a fitting property might be degraded.

In addition, in the disposable wearing article described above, if an attempt is made to enhance absorption performance of bodily liquid, it is considered to increase a thickness of the absorber. However, if the thickness of the absorber is increased, the absorber hardly curves, and a fitting property may be degraded. Alternatively, if an attempt is made to enhance absorption performance without increasing the thickness of the absorber, it is considered to increase a width of the absorber. However, if the width of the absorber is increased, an area of the absorber that is arranged in the crotch region increases, and it may be difficult to compactly dispose the absorber downward of the crotch portion. Therefore, there is an apprehension that a wearing property might be impaired due to a discomfort of the crotch unit, or alternatively, a side leakage might occur.

A disposable wearing article includes an absorber having a longitudinal direction, a widthwise direction perpendicular to the longitudinal direction, an inner direction for facing a wearer and an outer direction opposite the inner direction. The absorber has a crotch region that is adapted to be in contact with a crotch of the wearer, a front waistline region arranged anteriorly of the crotch region, and a back waistline region arranged posteriorly of the crotch region. A central curving unit that allows the absorber to curve in a convex shape in the inner direction is formed at a center in a widthwise direction of the crotch region. A first curving unit that allows the absorber to curve in a convex shape in the outer direction is formed in the crotch region and outboard of the central curving unit in the widthwise direction. A second curving unit that allows the absorber to curve in a convex shape in the inner direction is formed in the crotch region and outboard of the first curving unit in the widthwise direction. A concave unit is formed in the absorber to be concaved inwardly in the widthwise direction at an outside in the longitudinal direction relative to the first curving unit. The second curving unit is arranged outboard of an inside edge in the widthwise direction of the concave unit in the widthwise direction.

DESCRIPTION OF EMBODIMENTS

Figure 1:
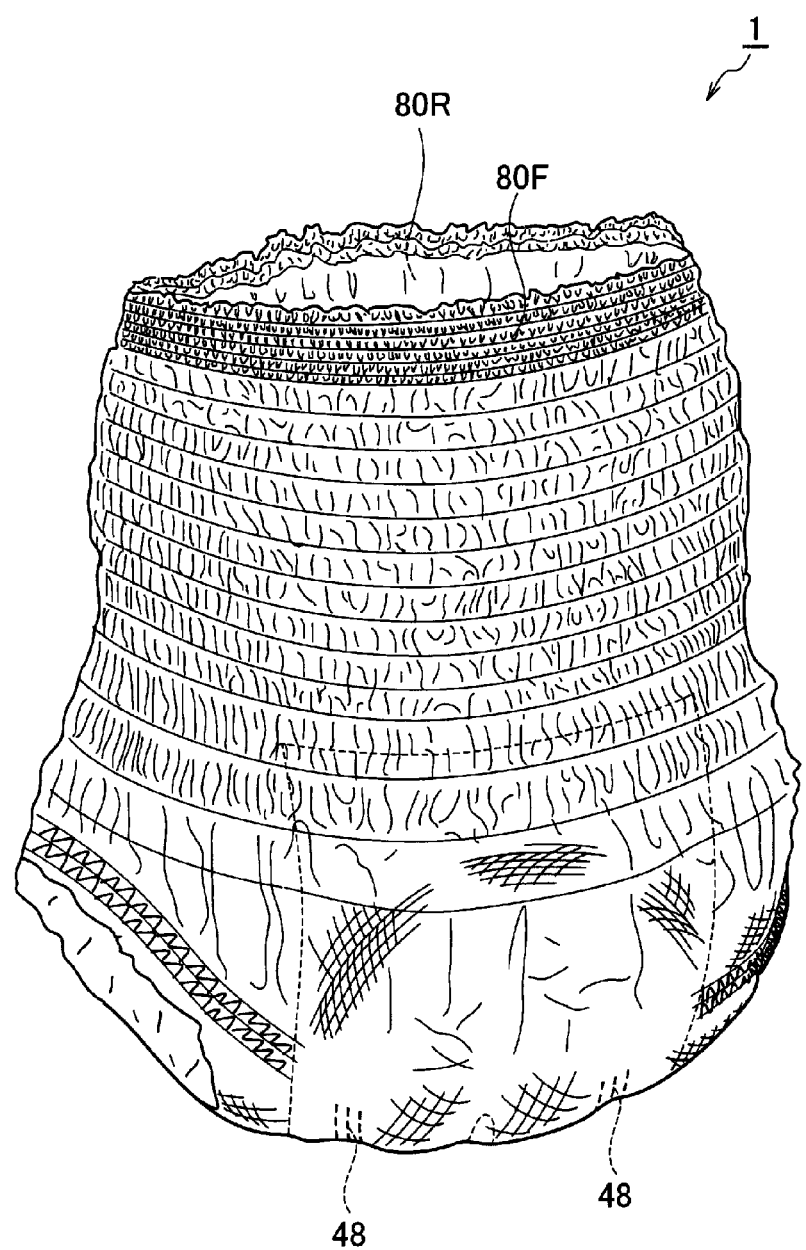
FIG. 1 is a schematic perspective view of a disposable diaper 1 according to at least one embodiment.

Next, embodiments of a disposable diaper 1 according to the present invention will be described with reference to the drawings. It is to be noted that in the following description of the drawings, same or similar constituent elements are designated by same or similar reference numerals. However, it should be kept in mind that the drawings are schematic representations and are not drawn to scale unless otherwise specified. Moreover, the drawings do not necessarily reflect the actual dimensional relationships and ratios of components. Therefore, specific dimensions or the like should be determined in consideration of the following description. In addition, relations or ratios among such dimensions may be different from one drawing to another.

An absorbent of a disposable wearing article, according to at least one embodiment, is characterized in that a central curving unit, a first curving unit, and a second curving unit, which are configured in such a manner as to enable the absorber to curve in a convex shape, and a concave unit which is concaved inwardly in the widthwise direction, are formed, and the second curving unit is positioned outboard of the inside edge of the concave unit in the widthwise direction.

(1) Overall Schematic Structure of Disposable Wearing Article

Figure 2:
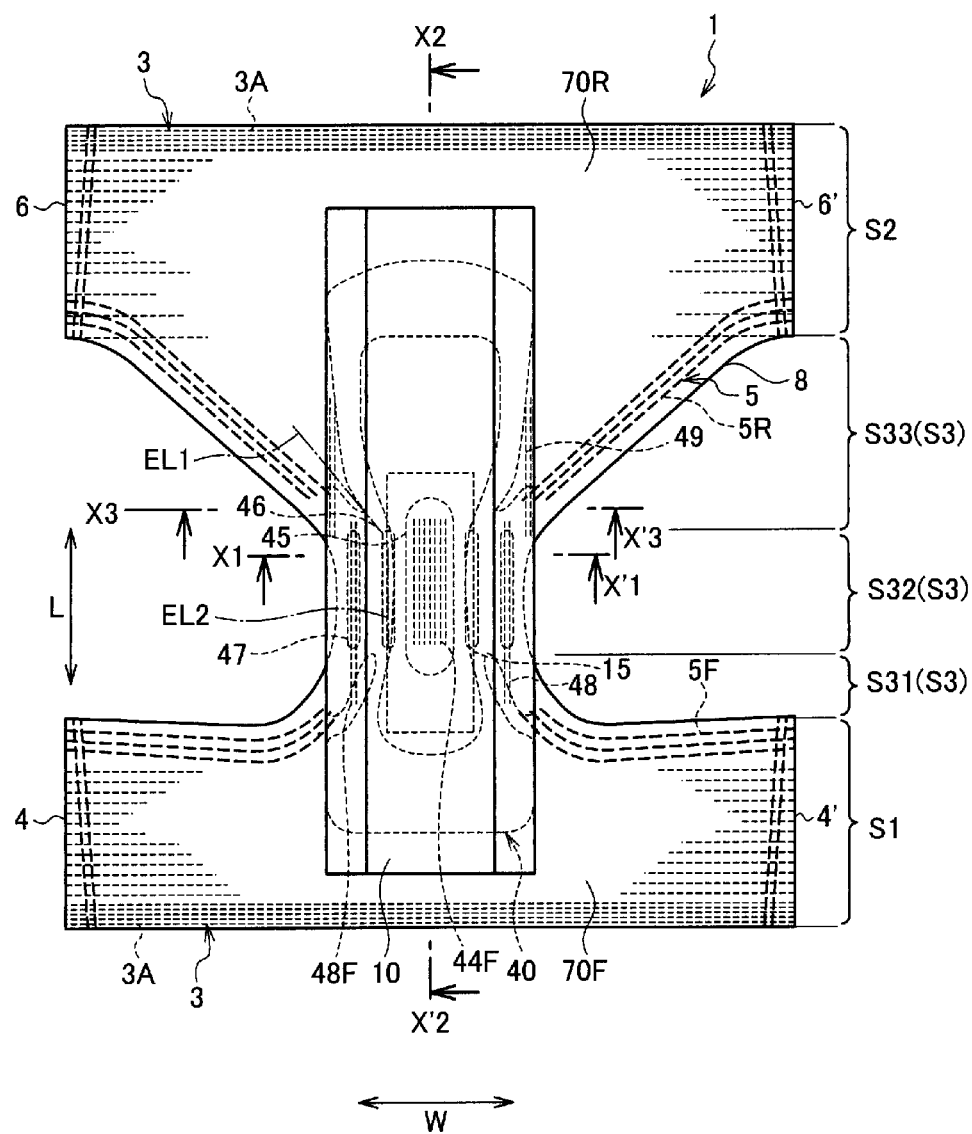
FIG. 2 is an exploded plan view of the disposable diaper of FIG. 1.
Figure 3:
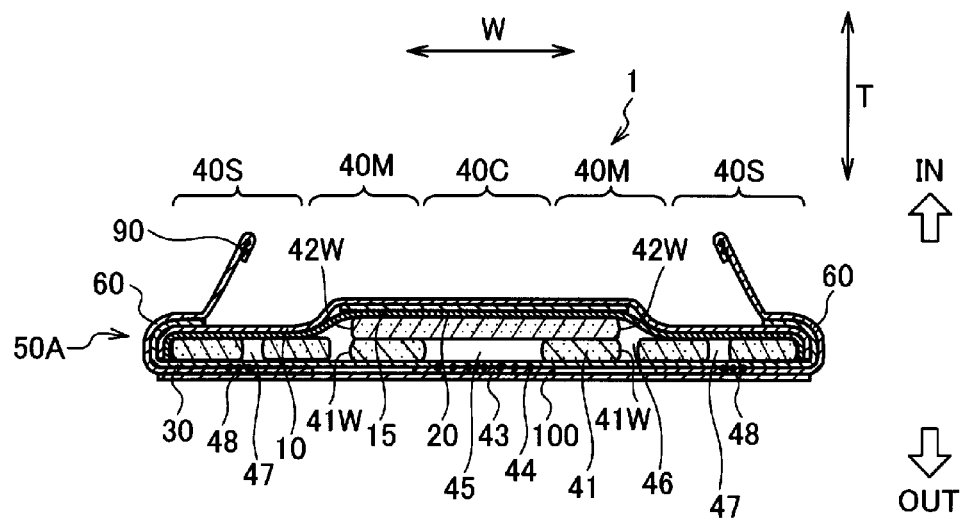
FIG. 3 is a cross section in a widthwise direction of the disposable diaper 1 taken along the line X1-X'1 shown in FIG. 2.
Figure 4:
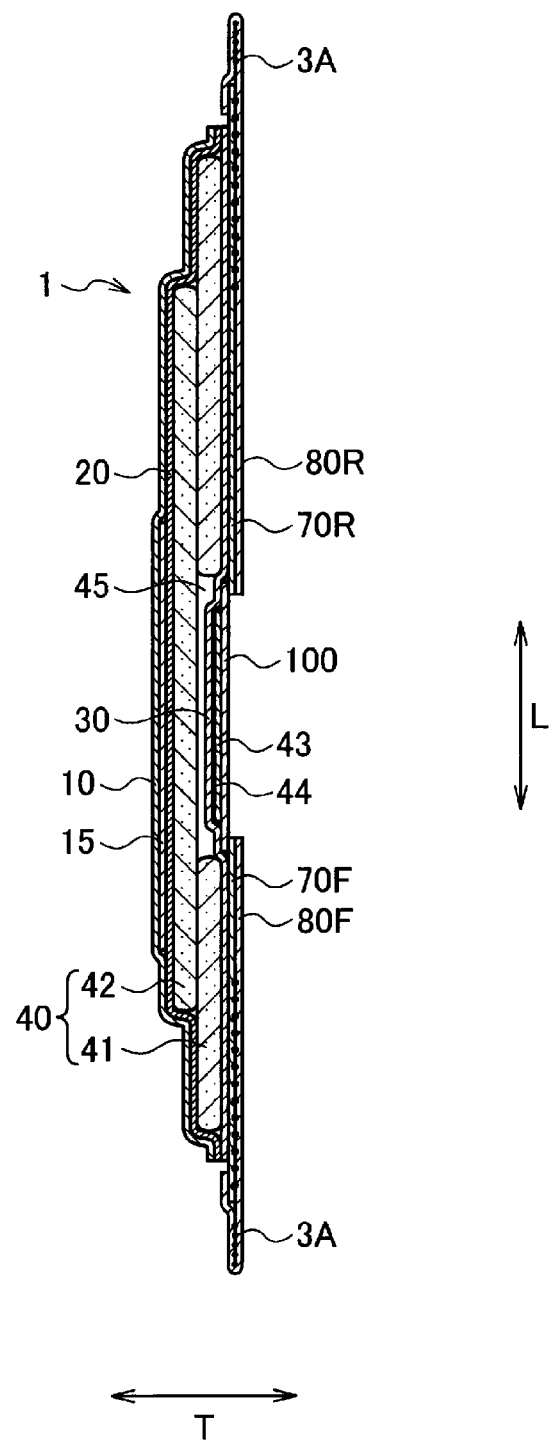
FIG. 4 is a cross section in a longitudinal direction of the disposable diaper 1 taken along the line X2-X'2 shown in FIG. 2.
Figure 5:
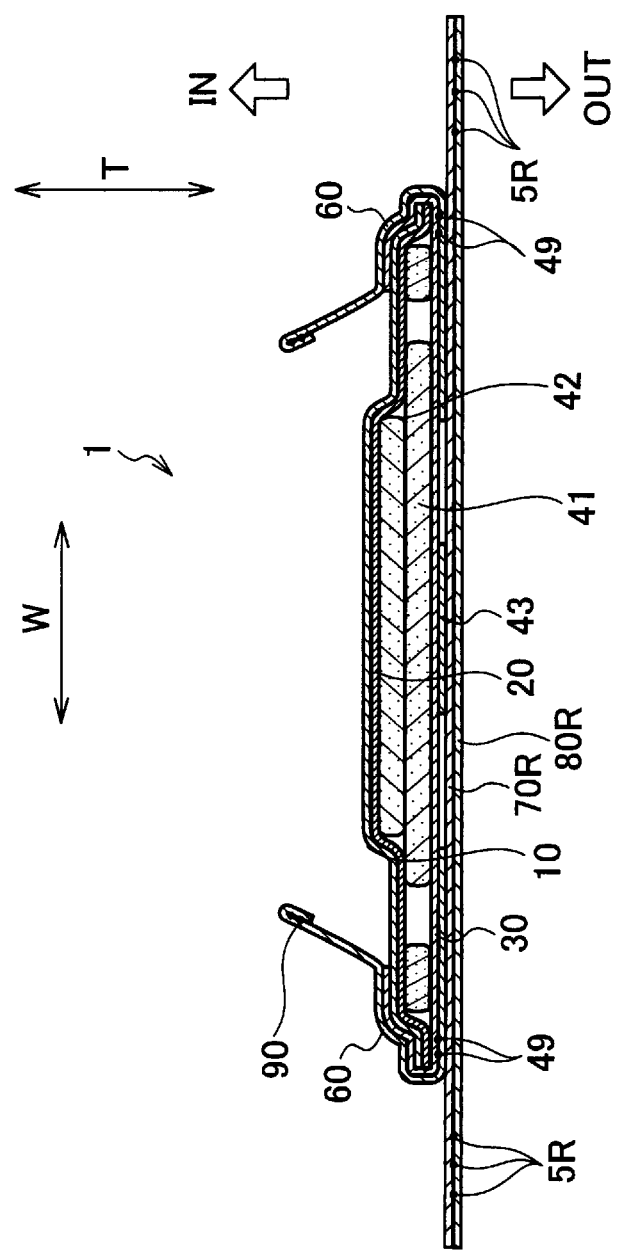
FIG. 5 is a cross section in a widthwise direction of the disposable diaper 1 taken along the line X3-X'3 shown in FIG. 2.

FIG. 1 is a schematic perspective view of a disposable diaper 1 forming a disposable wearing article in at least one embodiment. FIG. 2 is an exploded plan view of the disposable diaper 1 according to at least one embodiment. FIG. 3 is a cross section in a widthwise direction of the disposable diaper 1 taken along the line X1-X'1 shown in FIG. 2. FIG. 4 is a cross section in a longitudinal direction of the disposable diaper 1 taken along the line X2-X'2 shown in FIG. 2. FIG. 5 is a cross section in a widthwise direction of the disposable diaper 1 taken along the line X3-X'3 shown in FIG. 2. The disposable diaper 1 is a pants-type disposable diaper.

The disposable diaper 1, as shown in FIG. 2, has, in a longitudinal direction L of an absorbent article 1, a front waistline region S1 which corresponds to a front waistline of a wearer, a back waistline region S2 which corresponds to a back waistline of the wearer, and a crotch region S3 which corresponds to a crotch of the wearer, and is positioned between the front waistline region S1 and the back waistline region S2. The crotch region S3 has: a narrow region S32 which is the narrowest when legs are closed at the crotch portion of the wearer; a middle inside leg portion (abdominal side) S31 which is positioned between the narrow region S32 and the front waistline region S1; and a middle inside leg portion (hip side) S33 which is positioned between the narrow region S32 and the back waistline region S2.

Front waistline edges 4, 4' of the front waistline region S1 are joined with back waistline edges 6, 6' of the back waistline region S2, whereby a disposable diaper 1 is formed in a pants shape.

The disposable diaper 1 includes a topsheet 10, an absorber 40, a side sheet 60, a foreside exterior topsheet 70F, a backside exterior topsheet 70R, an exterior center sheet 100, a foreside exterior backsheet 80F, and a backside exterior backsheet 80R or the like, and these constituent elements are joined with each other by adhesive or hot-melt adhesive or the like.

The foreside exterior topsheet 70F, the backside exterior topsheet 70R, the foreside exterior backsheet 80F, the backside exterior backsheet 80R, and the exterior center sheet 100 are sheets which configure exterior portions of the disposable diaper 1. An absorber 40 made of a cotton-like pulp and a macromolecular water-absorptive polymer is provided at the inside (skin contact surface side) of the foreside exterior topsheet 70F, the backside exterior topsheet 70R, and the exterior center sheet 100.

The topsheet 10 is a sheet which forms a skin contact surface which is capable of directly bringing into contact with a wearer's skin. The topsheet 10 is formed of a liquid-permeable sheet such as a hydrophilic nonwoven cloth or textile stuff, an aperture plastic film, or an aperture hydrophobic nonwoven cloth. The topsheet 10 according to at least one embodiment is formed of a hydrophilic spun-bond nonwoven cloth of 20 g/m² in total weight made of polypropylene.

A second sheet 15 is joined with a non-skin contact surface side of the topsheet 10. The second sheet 15 is arranged between the topsheet 10 and an absorber top face covering sheet 20. The second sheet 15 is provided, whereby an absorption velocity of bodily liquid can be increased, and backflow of bodily liquid after absorbed can be restrained. Since the absorber of the absorbent article, according to at least one embodiment, is a structure coming into intimate contact with a wearer's crotch portion, comfort after excretion can be improved by restraining the backflow of bodily liquid after absorbed. As a material for the second sheet 15, for example, an air-through nonwoven cloth or a porous film or the like is employed. The second sheet 15 of at least one embodiment is formed of an air-through nonwoven cloth of 50 g/m² (hydrophilic).

Both side parts in the widthwise direction of the second sheet 15 are positioned to be substantially identical to those of a first side slit 46 (desirably inboard of the first side slit). A region in which the second sheet 15 is arranged is different in rigidity from a region in which no second sheet 15 is arranged (a region positioned outboard of edges of the second sheet 15 in the widthwise direction). By providing a difference in rigidity according to the presence or absence of the second sheet, curving is facilitated around the first curving unit made of a first side slit 46. It is to be noted that in at least one embodiment, a width of the first side slit 46 is 10 mm, an interval between inside edges in the widthwise direction of a pair of first side slits 46 is 76 mm, and a width of the second sheet is 80 mm.

The absorber top face covering sheet 20 is provided between the topsheet 10 and the absorber 40. The absorber top face covering sheet 20 is formed of a liquid-permeable sheet such as a hydrophilic nonwoven cloth or textile stuff, an aperture plastic film, an aperture hydrophobic nonwoven cloth, or tissue. An absorber back face covering sheet 30 is provided at a non-skin contact surface side of the absorber 40. The absorber back face covering sheet 30 is formed of a sheet such as a liquid-impermeable film (for example, polyethylene).

The absorber top face covering sheet 20 may be configured so as to be joined with the absorber back face covering sheet 30 at a portion at which the first side slit 46 is formed. The sheet is configured in this way, thereby making is possible to restrain the first side slit 46 from being closed, or alternatively, to restrain the absorber top face covering sheet 20 or the like and the absorber 40 from displaced, due to deformation of the absorber 40. In addition, in a case where the absorber 40 is swollen by absorbing a liquid, the closing of the first slit 46 can be prevented, thus making it possible to reliably form a convex-shaped portion by the first side slit 46.

The absorber 40 is arranged between the absorber top face covering sheet 20 and the absorber back face covering sheet 30. The absorber 40 has a longitudinal direction L from the front waistline region S1 toward the back waistline region S2 and a widthwise direction W which is orthogonal to the longitudinal direction L. Further, the absorber 40 has an inner direction IN arranged for facing a wearer who wears the disposable diaper 1, and an outer direction OUT opposites the inner direction. The absorber 40 is formed of mixed powder such as ground pulp and/or highly absorptive polymer.

Figure 7:
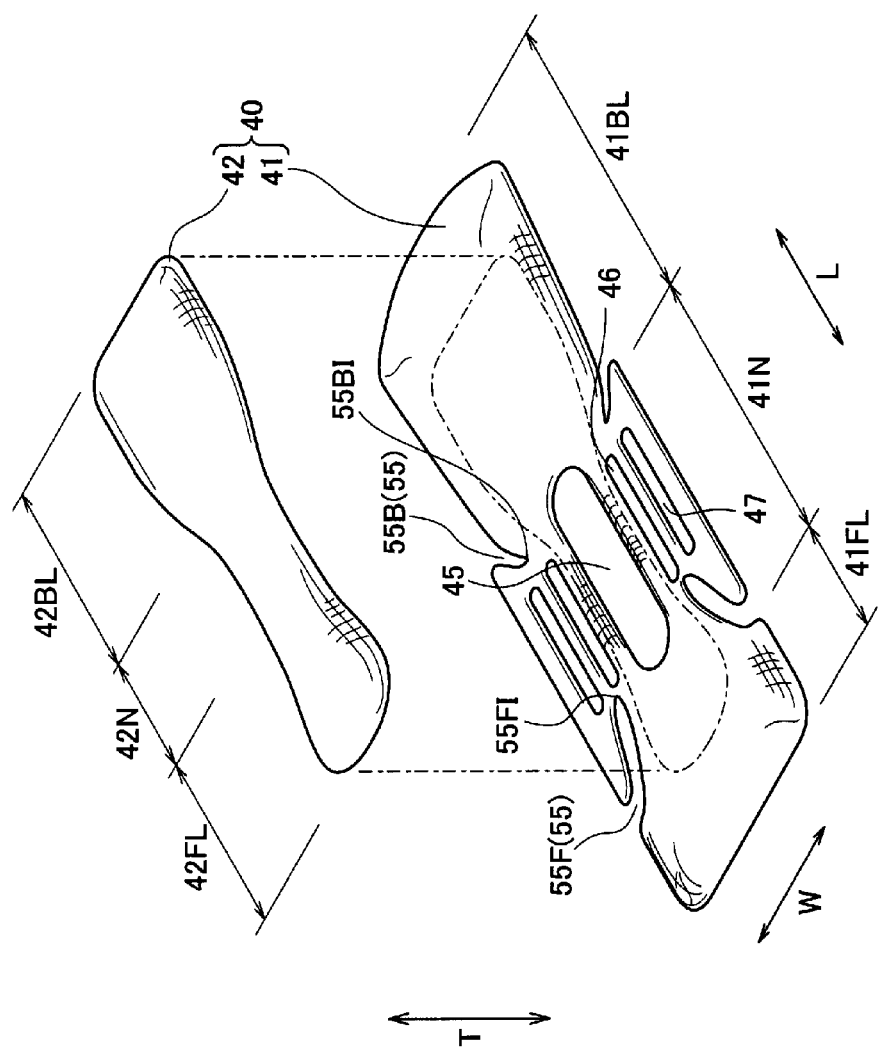
FIG. 7 is a perspective view of the absorber.

The absorber 40 is made of: a first layer 41 which is positioned at a non-skin contact surface side of the absorber; and a second layer 42 which is superimposed on the first layer 41, and is positioned at a skin contact surface side of the absorber (refer to FIG. 7). In the first layer 41 of the absorber 40, a central aperture (a central slit) 45 is formed at a center in the widthwise direction W. A pair of first side slits 46 are formed outboard of the central aperture 45 in the widthwise direction. A pair of second side slits 47 are formed outboard of the pair of first side slits 46 in the widthwise direction. A structure of the absorber 40 will be described later in detail.

The absorbent article 1 has: a central elastic member 44 which is arranged so as to be superimposed on a central aperture 45 in a thickness direction T of the absorbent article 1; and a slit elastic member 48 which is arranged so that at least part of the member is superimposed on the second side slit 47 in the thickness direction T.

As a result of the elastic members and slits formed in the absorber 40, the absorber 40 is configured such that it curves when the disposable diaper 1 is worn. In at least one embodiment, the central elastic member 44 and the central aperture 45 configure a central curving unit, the first side slit 46 configures a first curving unit, and the second side slit 47 and the slit elastic member 48 configure a second curving unit.

A side sheet 60 is provided so as to integrally envelope the topsheet 10, the absorber top face covering sheet 20, and the absorber back face covering sheet 30 at both side ends in the widthwise direction W of the absorber 40. The side sheet 60 is made of a sheet such as a liquid-impermeable nonwoven cloth, and a leakage-proof wall for preventing a side leakage of excretions is made of the side sheet 60 and the side elastic member 90.

The exterior topsheet includes: a foreside exterior topsheet 70F which is formed in the front waistline region S1 and the middle inside leg portion (abdominal side) S31; and a backside exterior top sheet 70R which is formed in the back waistline region S2 and the middle inside leg portion (hip side) S33. In the thickness direction T, the exterior top sheet 70F is arranged between the foreside exterior back sheet 80F and the absorber 40. In the thickness direction T, the backside exterior top sheet 70R is arranged between the backside exterior backsheet 80R and the absorber 40. In the longitudinal direction L, the exterior center sheet 100 is arranged between the foreside exterior top sheet 70F and the backside exterior top sheet 70R.

A front edge of the exterior center sheet 100 is joined with a back edge of the foreside exterior topsheet 70F, and a back end part of the exterior center sheet 100 is joined with a front end part of the backside exterior topsheet 70R. The exterior center sheet 100 is arranged across the foreside exterior top sheet 70F and the backside exterior topsheet 70R. The exterior center sheet 100 is joined with a top face side of the exterior topsheet by hot-melt adhesive which is continuously applied by means of a slot coater.

The exterior center sheet 100 is made of a nonwoven cloth or the like. The exterior center sheet 100 according to at least one embodiment is made of an SMS (spun bond-meltblown-spun bond) nonwoven cloth of 15 g/m² in total weight made of polypropylene. When wearing the disposable diaper 1, the exterior center sheet 100 is positioned inboard of the exterior topsheet (at the skin contact surface side).

The foreside exterior topsheet 70F and the backside exterior topsheet 70R are formed with a width in the widthwise direction W that is longer than that of any other region in the front waistline region S1 and the back waistline region S2. The foreside exterior topsheet 70F and the backside exterior topsheet 70R can be formed of an air-through nonwoven cloth, a spun bond nonwoven cloth, an SMS nonwoven cloth, or a waterproof film or the like. The exterior top sheet according to at least one embodiment is made of an SMS nonwoven cloth of 15 g/m² in total weight made of polypropylene.

The foreside exterior backsheet 80F is provided at the non-skin contact surface side more than the foreside exterior topsheet 70F in the front waistline region S1. The backside exterior backsheet 80R is provided at the non-skin contact surface side more than the backside exterior topsheet 70R in the back waistline region S2. One end of the foreside exterior backsheet 80F (backside exterior backsheet 80R) in the longitudinal direction L is folded back to the skin contact surface side, and is provided so as to envelope an end part in the longitudinal direction L of the foreside exterior topsheet 70F (backside exterior topsheet 70R).

The foreside exterior backsheet 80F and the backside exterior backsheet 80R can be formed of an air-through nonwoven cloth, a spun bond nonwoven cloth, an SMS nonwoven cloth, or a waterproof film or the like. The foreside exterior backsheet 80F and the backside exterior backsheet 80R, according to at least one embodiment, are made of a spun bond nonwoven cloth of 17 g/m² in total weight made of polypropylene.

The absorber back face covering sheet 30 is partially bonded with the foreside exterior topsheet 70F, the backside exterior topsheet 70R, and the exterior center sheet 100.

A waist gather 3 is provided in the front waistline region S1 and the back waistline region S2. The waist gather 3 has an elongated waist elastic member 3A, such as a synthetic rubber, which is arranged so as to expand or contract along the widthwise direction W of the absorber 40. The waist elastic member 3A is joined between the foreside exterior topsheet 70F and the foreside exterior backsheet 80F and between the backside exterior topsheet 70R and the backside exterior backsheet 80R by means of an adhesive (for example, hot-melt adhesive) in a state in which the elastic member is expanded relative to the widthwise direction W of the disposable diaper 1.

The waist gather 3 is continuous from one front waistline edge 4 up to the other waistline edge 4' of the front waistline region S1, and is also continuous from one back waistline edge 6 up to the other front waistline edge 6' of the back waistline region S2.

Leg gathers 5 are formed in the middle inside leg edge 8 of the backside exterior backsheet 80R. The leg gathers 5 are formed so as to run around the legs of a wearer. The leg gather is formed of an elongated leg-line elastic member 5, such as a synthetic rubber, which is arranged so as to expand or contract. The leg-line elastic member 5 is made of a front leg-line elastic member 5F, which is arranged from the front waistline region S1 to the middle inside leg portion (abdominal side) S31, and a back leg-line elastic member 5R, which is arranged from the back waistline region S2 to the middle inside leg portion (hip side) S33.

The leg-line elastic member 5 is joined between the foreside exterior topsheet 70F and the foreside exterior backsheet 80F and between the backside exterior topsheet 70R and the backside exterior backsheet 80R. The back leg-line elastic member 5R extends from the back waistline edge 6 up to the middle inside leg portion (hip line) S33, and is divided just before reaching the narrow region S32. The front leg-line elastic member 5F extends from the front waistline edge 4 up to the middle inside leg portion (hip side) S31, and is divided just before reaching the narrow region S32.

The front leg-line elastic member 5F and the back leg-line elastic member 5R that form a leg gather are divided by cutting an elastic member at a site which comes out of a crotch edge of the foreside exterior topsheet 70F (backside exterior topsheet 70R) and the foreside exterior backsheet 80F (backside exterior backsheet 80R) before the exterior center sheet 100 is joined with the foreside exterior topsheet 70F (backside exterior topsheet 70R), for example.

The leg-line elastic member 5 is fixed by hot-melt adhesive that is applied to an exterior topsheet in advance. An application quantity of the leg-line elastic member 5 was determined at 7 g/m². An adhesive agent is applied by means of a slot coater for at least a position superimposed on the leg-line elastic member 5 in the vicinity of an edge of an exterior topsheet (at a position which is about 5 mm from the edge of the exterior topsheet). An adhesive agent is applied in this way, thereby making it possible to prevent the leg-line elastic member 5 from slipping off from the edge of the exterior topsheet.

In addition, if an adhesive agent is applied by means of a noncontact-type spiral spray, an adhesive agent in the vicinity of the edge of the exterior topsheet comes out, and there is an apprehension that a manufacturing failure might occur. However, an adhesive agent is applied by means of a contact-type slot coater, thereby making it possible to prevent overflow of the adhesive agent. The application quantity of the slot coater was determined at 10 g/m².

At edges in the widthwise direction of the side sheets 60, the side sheets are superimposed on each other. At a portion at which the side sheets are superimposed on each other, a side elastic member 90 (refer to FIG. 3) is provided in a state in which the elastic member extends along the longitudinal direction L. The side elastic member 90 is continuous from the middle inside leg portion (hip side) S33 up to the middle inside leg portion (abdominal side) S31 through the narrow region S32. The side elastic member 90 is formed of a synthetic rubber having elasticity.

A central elastic member 44 is provided along the longitudinal direction L, and is provided at a position at which the central elastic member 44 is superimposed on a central aperture 45 in the thickness direction T of the disposable diaper 1. The central elastic member 44 is formed so that the absorber 40 convexly curves in an inner direction IN. The central elastic member 44 is arranged in an extended state along the longitudinal direction at a center in the widthwise direction of the absorbent article. The central elastic member 44 is arranged from the middle inside leg portion (abdominal side) S31 toward the middle inside leg portion (hip side) S33 around the narrow region S32.

A slit elastic member 48, in the longitudinal direction L, is provided at a position at which the slit elastic member 48 is superimposed on a second side slit 47 in the thickness direction T of the disposable diaper 1. A total of three slit elastic members 48 are arranged in a parallel state in the widthwise direction W. The slit elastic members 48 are formed so as to be superimposed on the absorber 40 along the longitudinal direction L so that the absorber 40 curves in a convex shape toward a wearer.

The central elastic member 44 is provided in an expanded state between an elastic member covering sheet 43 and an absorber back face covering sheet 30. The central elastic member 44 is arranged at an expansion magnification of 1.2 times to 2.5 times. A total of seven central elastic members according to at least one embodiment are fixed in an expanded state at a thickness of 62 dtex and at an expansion magnification of 1.8 times. Intervals between these central elastic members are 5 mm, respectively. A length in the longitudinal direction L of each of the central elastic members 44 is about 120 mm.

The central elastic member 44 is a spandex, and a hot melt-type adhesive agent is applied thereto in a V-slot system. An expandable nonwoven cloth or the like may be employed for a material for the central elastic member 44. An elastic member covering sheet 43 is made of a sheet such as a nonwoven cloth, and in at least one embodiment, an SMS nonwoven cloth (hydrophobic) of 15 g/m² in total weight made of polypropylene was employed.

The slit elastic member 48 is joined by an adhesive between the absorber back face covering sheet 30 and the side sheet 60. A total of two slit elastic members 48 according to at least one embodiment are fixed in an expanded state at a thickness of 620 dtex and at an expansion magnification of 2.0 times. The slit elastic member 48 is a spandex. A hot melt-type adhesive agent is applied to the slit elastic member 48 by a direct coating method with slit nozzle coating.

It is to be noted that the slit elastic member 48 is formed to obtain an expansion stress which is lower than that of the central elastic member 44 in a state before the absorber 40 curves in a convex manner. The state before the absorber curves in the convex manner is, in other words, a state in which a wearing article shown in FIG. 2 is extended in a plane. The slit elastic member 48 is configured so as to obtain an expansion stress which is lower than that of the central elastic member 44, whereby a height of a convex-shaped portion which is formed by the central elastic member 44 is more than that of a convex-shaped portion which is formed by the slit elastic member 48. Therefore, it becomes possible to bring the convex-shaped portion formed by the central elastic member 44 and/or the convex-shaped portion formed by the slit elastic member 48 into intimate contact with an excretion portion of the wearer at the time of wearing.

A front edge 44F of the central elastic member 44 is arranged posteriorly of a front edge 48F of the slit elastic member 48. That is, the front edge of a central curving unit is arranged posteriorly of the front edge of a second curving unit. According to such a structure, a space is easily formed in a foreside of a wearer at a crotch portion, making it possible to inhibit the deterioration in the comfort when worn by the fact that the foreside of the crotch portion is compressed.

A material for the central elastic member 44 and the slit elastic member 48 can include a synthetic rubber made of styrene-butadiene, butadiene, isoprene, neoprene or the like, a natural rubber, EVA, expandable polyolefin, spandex, foamed polyurethane or the like, for example. As another material for the central elastic member 44 and the slit elastic member 48, there may be employed an elastic sheet such as an expandable nonwoven cloth.

Side edge elastic members 49 are bonded by an adhesive between the absorber back face covering sheet 30 and the side sheet 60 at both side parts in the widthwise direction of the absorber. The side edge elastic member 49 is arranged along the longitudinal direction L, and is arranged across the middle inside leg portion (hop side) S33 and the narrow region S32 of the crotch region S3. The side edge elastic member 49 is arranged posteriorly of the slit elastic member 48 in the longitudinal direction and outboard of the slit elastic member 48 in the widthwise direction. The side edge elastic member 49 serves to pull up a side part of the absorber that is arranged posteriorly of the narrow region, and deform the absorber so as to envelope a hip of a wearer. By deforming the absorber in this way, a leakage from the middle inside leg portion (hip portion) can be prevented. A total of two side edge elastic member 49 according to at least one embodiment is fixed in an expanded state at a thickness of 780 dtex and at an expansion magnification of 2.3 times.

The expansion stress of the elastic member can be measured as described below, for example.

(1) The material holding the elastic members in between is cut such that all the elastic members forming the convex-shaped portion(s) are included in the widthwise direction. More specifically, from the wearing article according to at least one embodiment, a test piece of 13-mm width×100-mm length that hold the three central elastic members or the three first elastic members arranged in an interval of 5 mm, in an elongated state such that there is no sagging, is cut out. In the elongated state, a mark is put at 10 mm from either end in the longitudinal direction of the test piece. A tensile tester made by Instron Japan Co., Ltd. (for example, model No. 5564) or an autograph made by Shimadzu Corporation (for example, model No. AGS-1kNG) can be used to measure the elongation stress.

(2) The test piece prepared at (1) is held in between the upper chuck, such that one of the marks is at the inner end of the upper chuck, and the lower chuck, such that the other mark is at the inner end of the lower chuck. The length of the test piece between the chucks is 80 mm. Note that if the effective length of the gathers of the elastic member is less than 100 mm, a length that is 20 mm shorter than the shortest length from among the effective lengths of the gathers of the elastic members is set as the length of the test piece between the chucks. The initial distance between chucks is set shorter than the length (natural length) when the test piece is relaxed such that no external tension is exerted on the test piece. In order to be alienated from each other, the chucks pull the test piece in the vertical direction under a condition of 100 mm/min, and elongate the test piece.

(3) By assuming the length of the test piece between the chucks as 100% when the material holding the elastic members in between is elongated without any sagging, the test piece is elongated from the initial distance until its length between the chucks becomes 90%, and then the elongation stress of the test piece is measured for that point of time and set as the stress of the elastic member. That is, in the above embodiment, the elongation stress is measured when the test piece is elongated until its length becomes 90% that is 72 mm, of the 100% length of 80 mm.

The thickness of the absorber 40 is measured by holding the portion to be measured in the thickness measuring gauge in a state when it has been extended to the product length and product width of the absorber 40 (that is, in a flat state such that no creases are formed). A thickness gauge manufactured by PEACOCK (measuring portion: 5-mm diameter, pressure during measurement: 163 $g/cm^2$), for example, can be used as the usable measurement device.

Note that each member configuring the disposable diaper 1 may, for example, use the respective materials described in the Japanese Published Unexamined Application No. 2006-346439, which is incorporated by reference herein in its entirety.

(2) Structure of Absorber

Figure 6:
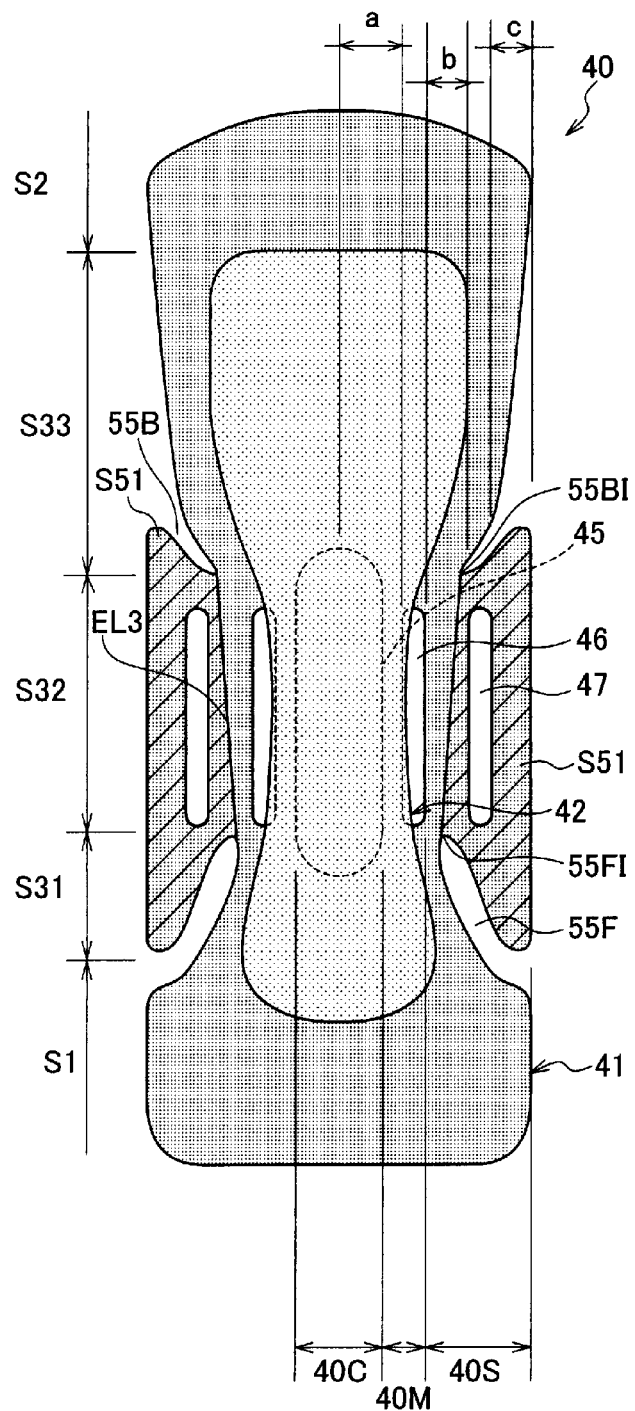
FIG. 6 is a plan view of an absorber according to at least one embodiment.

FIG. 6 is a plan view of the absorber 40 and FIG. 7 is an exploded, perspective view of the absorber 40. As shown in FIG. 6 and FIG. 7, the absorber 40 has a first absorbent layer (also referred to herein as first layer) 41, and a second absorbent layer (also referred to herein as second layer) 42 overlapping the first layer 41. The first layer 41 is positioned at the non-skin contact surface side of the wearer, and the second layer 42 is positioned at the skin contact surface side of the wearer. A length in a longitudinal direction of the first layer 41 is longer than a length in a longitudinal direction of the second layer 42. The first layer 41 is arranged from a front waistline region S1 across a back waistline region S2.

The first layer 41 and the second layer 42 are configured by cotton-like pulp and highly polymerized water absorbent polymer (SAP). The absorber 40 is formed by mixing a pulp of 0 to 500 $g/m^2$ and an SAP of 0 to 500 $g/m^2$ with each other, or is formed by either a pulp or an SAP for example. The first layer 41 is formed by mixing a pulp of 250 $g/m^2$ and an SAP of 150 $g/m^2$ with each other, a thickness of which is about 2.5 mm in a particular configuration. The second layer 42 is formed by mixing a pulp of 200 $g/m^2$ and an SAP of 90 $g/m^2$ with each other, a thickness of which is about 2.0 mm in a particular configuration.

The second layer 42 has: a narrow part 42N which is concave toward a center in the widthwise direction W, and has a predetermined width in the widthwise direction W; and a wide part 42FL and a wide part 42BL which are formed at both ends of the narrow part 42N in the longitudinal direction L, each of which has a longer width than a width of the narrow portion. The narrow part 42N is formed in the narrow region S32 of the crotch region S3. The wide part 42FL is formed at a middle inside leg portion (abdominal side) S31, and the wide part 43BL is formed at a middle inside leg portion (hip side) S33. A side end of the narrow part 42N, a side end of the wide part 42FL, and a side portion of the wide part 42BL are connected by a curve, and the second layer 42 has an hourglass-type flat shape.

The first layer 41 has a smaller width in the widthwise direction from the middle inside leg portion (abdominal side) S31 toward the narrow region S32, and has a smaller width in the widthwise direction from the middle inside leg portion (hip side) S33 toward the narrow region.

At the middle inside leg portion (abdominal side) S31 and the middle inside leg portion (hip side) S33 of the first later 41, a concave unit 55 is formed in such a shape that the concave unit is concaved inwardly in the widthwise direction. The concave unit 55 has: a foreside concave portion (a first concave portion) 55F which is arranged anteriorly of the narrow region S32 and to be arranged anteriorly of a first side slit 46 forming a first curving unit; and a back concave portion (a second concave portion) 55B which is positioned to be more backward than the narrow region S32 and to be more backward than the first side slit 46. The foreside concave portion 55F is formed in a shape backwardly extending in the longitudinal direction and inwardly in the widthwise direction, and the backside concave portion 55B is formed in a shape forwardly extending in the longitudinal direction and inwardly in the widthwise direction.

In the first layer 41, a central aperture 45, a pair of first side slits 46, and a pair of second side slits 47, are formed. The central aperture 45 is formed at a center part in the widthwise direction W. The central aperture 45 is formed in a longitudinally elongated shape extending along the longitudinal direction L, and is formed across the narrow region S32, the middle inside leg portion (abdominal side) S31, and the middle inside leg portion (hip side) S33. By forming the central aperture 45 this way, a central portion 40C can be easily curved in a convex shape in an inner direction IN toward a wearer. Furthermore, by increasing the diffusibility of the bodily fluid in the front-back (longitudinal) direction of the absorber and by diffusing the bodily fluid in a wide range, the absorption performance can be improved.

The first side slit 46 and the second side slit 47 are positioned outboard of the central aperture 45 in the widthwise direction. The first side slit 46 and the second side slit 47 has a longitudinally elongated shape extending along the lengthwise direction L, and are positioned in the narrow region S32.

A pair of first side slits 46 are formed in the absorber 40 along the longitudinal direction L so that the absorber 40 curves in a convex shape in an outer direction OUT, namely in an opposite direction to that of the central aperture 45. A pair of second side slits 47 are formed in the absorber 40 along the longitudinal direction L so that the absorber 40 curves in a convex shape in an inner direction IN, namely in the same direction as that of the central aperture 45.

The first side slit 46 is arranged in the widthwise direction to be inward of widthwise inside edges 55FI and 55BI of the foreside concave portion 55F and the backside concave portion 55B. The second slide slit 47 is arranged in the widthwise direction to be outward of the widthwise inside edges 55FI and 55BI of the foreside concave portion 55F and the backside concave portion 55B.

The absorber 40 has an extension region S51 which is positioned between the foreside concave portion 55F and the backside concave portion 55B in the longitudinal direction. The extension region S51 is a region which extends in the widthwise direction to be outward of a virtual line EL3 connecting an inside edge in the widthwise direction of the foreside concave portion 55F and an inside edge in the widthwise direction of the backside concave portion 55B to each other. The first side slit 46 is arranged in the widthwise direction to be inward of the extension region S51, and the second side slit 47 is arranged in the widthwise direction to be outward of the extension region S51. The extension region S51 is a region which is shaded in FIG. 6.

In the extension region S51, a second side slit 47 forming a second curving unit is formed. A slit elastic member 48 forming the second curving unit is arranged on a non-skin contact surface side of the second side slit 47. Therefore, the extension region S51 is formed to be convexly curved in an inner direction by the second curving unit.

A concave unit 55 is formed at the outside in the longitudinal direction of the first side slit 46 forming a first curving unit, thus making it possible to hardly transmit a deformation exerted by the first curving unit to the outside in the longitudinal direction. Therefore, a portion of the absorber, which is positioned outboard of the first curving unit in the longitudinal direction, is restrained from being deformed in a convex shape, making it possible to dispose the portion of the absorber along a wearer's skin. In addition, even in a case where the front waistline region S1 and the back waistline region S2 of the absorber are deformed, such deformation is hardly transmitted to the crotch region, thus making it possible to stably fold the crotch region in a convex shape.

In addition, since the concave unit 55 is formed in the absorber 40, for example, even in a case where an area of the absorber is increased in order to ensure absorption performance, the absorber 40 in the crotch region S3 is appropriately folded back, enabling the absorber 40 and an excretion portion of the wearer to come into intimate contact with each other. Therefore, the discomfort of the crotch unit can be reduced while absorption performance is ensured.

Further, the extension region S51 is formed in a shape which extends outwardly in both the longitudinal direction and the widthwise direction. This region is configured in such a manner that a maximum length in the longitudinal direction of the extension region S51 located outward of the virtual line EL3 is longer than a length of the virtual line EL3 in the longitudinal direction. As described above, the virtual line EL3 is a virtual line connecting an inside edge in the widthwise direction of the foreside concave portion 55F and an inside edge of the backside concave portion 55B to each other. Therefore, since the extension region S51 is formed in a shape expanding outwardly in the widthwise direction and the region is also formed to be curved in a convex shape, it is possible to increase an area of an absorber which is arranged at a wearer's crotch portion, and to enhance absorption performance.

A first virtual line EL1 (refer to FIG. 2) which connects an outside edge in the widthwise direction of the concave unit and an inside edge in the widthwise direction of the concave unit to each other is configured so as to cross a second virtual line EL2 along a first side slit 46. By forming the concave unit in this way, the absorber 40 is configured so as to curve along the skin contact surface side on a border of the virtual line EL1 connecting the first side slit 46 which serves as the first curving unit and the concave unit to each other. The concave unit may be formed in a shape which extends outwardly in the longitudinal direction, or alternatively, may be formed in a shape which extends outwardly in the widthwise direction.

In at least one embodiment, a width of the absorber is 120 mm to 250 mm in the front waistline region S1 and the back waistline region S2, and 120 mm to 250 mm in the crotch region S3 (e.g., in the extension region S51). A width of the absorber according to at least one embodiment is 196 mm in any region as well.

A length in the longitudinal direction of the central aperture 45 is longer than a length in the longitudinal direction of the first side slit 46, and is longer than a length in the longitudinal direction of the second side slit 47. A width in the widthwise direction of the central aperture 45 is longer than a width in the widthwise direction of the first side slit 46, and is longer than a width in the widthwise direction of the second side slit. In at least one embodiment, a width of the central aperture is 40 mm, and the widths of the first and second side slits are 10 mm, respectively.

In at least one embodiment, when a distance from a center in the widthwise direction of the central aperture 45 to an inside edge in the widthwise of the first side slit 46 was assumed to be a, a distance from an outside edge in the widthwise direction of the first side slit 46 to an inside edge in the widthwise direction of the second side slit 47 was assumed to be b, and a distance from an outside edge in the widthwise direction of the second side slit 47 to an outside edge in the widthwise direction of the absorber was assumed to be c, these distances were defined as a=38 mm, b=20 mm, and c=20 mm, respectively.

That is, a distance in the widthwise direction between a central elastic member 44, which configures a central curving unit, and the first side slit 46 that configures a first curving unit, is longer than a distance in the widthwise direction between the first side slit 46 and the second side slit 47 that configures a second curving unit. Therefore, a height of a convex-shaped portion formed by the central curving unit is greater than a height of a convex-shaped portion formed by the second curving unit. Thus, at the time of wearing the disposable diaper 1, the convex-shaped portion formed by the central curving unit toward a wearer's excretion portion easily comes into contact with the excretion portion. In addition, since the first curving unit forms a concave-shaped portion, excretion easily gets into the concave-shaped portion, making it possible to restrain a wearer's skin and bodily waste from coming into direct contact with each other.

In at least one embodiment, a difference between a and b and a difference between a and c are preferably at least 3 mm, respectively, and is further preferably 7 mm to 25 mm. In at least one embodiment, a difference between a and b and a difference between a and c are 18 mm, respectively. For example, in a case where the difference is small, e.g., less than 7 mm, the absorber is hardly lifted upward, and a center in the widthwise direction of the absorber may hardly come into intimate contact with the wearer's crotch. On the other hand, in a case where the difference is large, e.g., greater than 25 mm, bodily liquid might easily flow from the center in the widthwise direction of the absorber outwardly in the widthwise direction, and there is an apprehension that a side leakage might occur.

In the crotch region S3, an outside edge 42W in the widthwise direction of the second layer 42 is arranged along the longitudinal direction. The portion of the absorber 40 outboard of the outside edge 42W is made of only the first layer 41, and the portion of the absorber 40 inboard of the outside edge 42W is made of both the first layer 41 and the second layer 42 except for a portion at which the central aperture 45 is formed. Therefore, the rigidity and thickness of the absorber 40 vary on a boundary of the outside edge 42W of the second layer 42. In at least one embodiment, the absorber curves on the boundary of the outside edge 42W of the second layer of which rigidity or the like varies.

The outside edge 42W of the second layer 42 is superimposed in the thickness direction on the edge 41W of the first layer in which the first side slit 46 is formed. The absorber curves in a convex shape toward an outer direction around the outside edge 42W of the first layer 42 and the edge 41W of the first layer. It is to be noted that the outside edge 42W in the widthwise direction of the second layer 42 and the edge 41W of the first layer are edges along the longitudinal direction. Therefore, the first curving unit is formed along the longitudinal direction.

The absorber 40 made of the first layer 41 and the second layer 42, as shown in FIG. 3, has a central portion 40C, an intermediate portion 40M, and a side end portion 40S. The central portion 40C is formed at a central part of the absorber 40 in the widthwise direction W. The intermediate portion is positioned between the central portion 40C and the side end portion 40S. A convex-shaped portion exerted by the central curving unit is formed at the central portion 40C. A convex-shaped portion exerted by the first curving unit is formed at the intermediate portion 40M. A convex-shaped portion exerted by the second curving unit is formed at the side end portion.

In at least one embodiment, the first layer 41 and the second layer 42 are compressed in the thickness direction T to be thereby integrated with each other. It is to be noted that the first layer 41 and the second layer 42 may be integrated with each other by an adhesive or hot-melt adhesive. In addition, while, in the absorber 40, the first layer 41 is positioned at a non-skin contact surface side, and the second layer 42 is positioned on a skin contact surface side, the second layer 42 may be positioned at the non-skin contact surface side, or alternatively, the first layer 41 may be positioned at the skin contact surface side.

(3) Shape Change of Absorber

Figure 8:
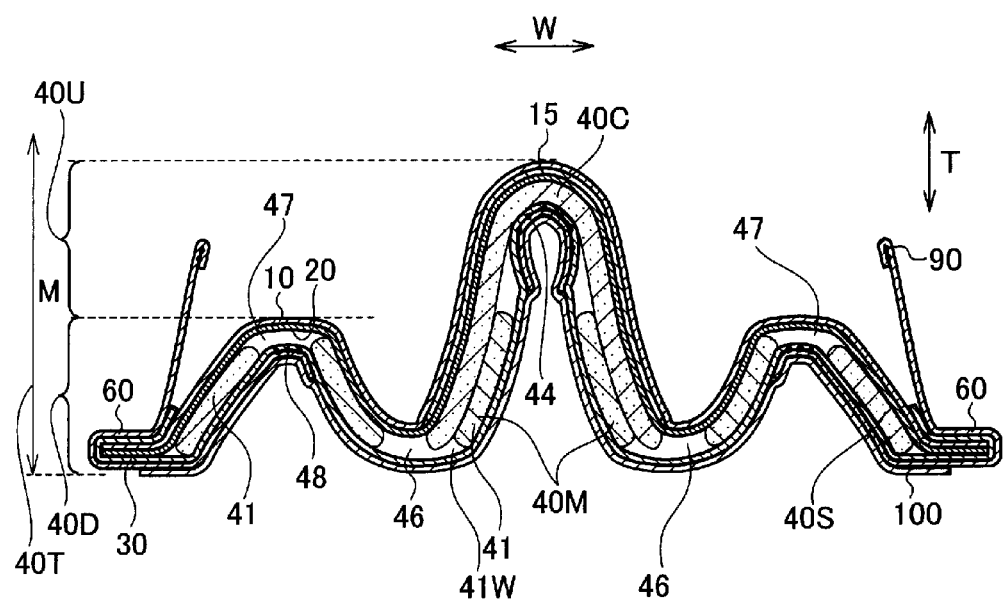
FIG. 8 is a cross section taken along the line X1-X'1, schematically showing a state in which the disposable diaper 1 according to at least one embodiment is worn.

FIG. 8 is a cross section schematically showing a state in which a disposable diaper 1 is worn (taken along the line X1-X'1 of FIG. 1). As shown in FIG. 8, when the disposable diaper 1 is worn, a crotch region S3 of the absorber is abutted against a crotch portion of a wearer. By the wearer's legs or the like, a force is applied to the absorber inwardly in the widthwise direction. As far as the absorber 40 is concerned, the absorber 40 curves around a central elastic member 44 and a central aperture 45, a first side slit 46, and a second side slit 47 and a slit elastic member 48, and the sectional shape taken along a widthwise direction W of the disposable diaper 1 is deformed in a wavy shape. Therefore, a narrow region S32 of a crotch region S3 of the absorber 40 is established in a regularly folded state.

In the absorber 40, a top face of the absorber 40 formed in a convex shape in an inner direction IN by the central elastic member 44 abuts against a wearer's crotch portion. In addition, a central portion 40C is positioned in an upper region 40U which is closer to a wearer's body than a virtual line M which bisects a height 40T of the absorber 40 in the deformed state. On the other hand, an intermediate portion 40M and a side end portion 40S are positioned in a lower region 40D which is spaced farther from the wearer's body than the virtual line M.

A central portion 40C in which a convex-shaped portion is formed by the central curving unit is configured only by a second layer 42, and its thickness is comparatively less. In a region between the convex-shaped portion formed by the central curving unit in the intermediate portion 40M and a convex-shaped portion formed by the first curving unit, the first layer 41 and the second layer 42 are overlapping, and its thickness is comparatively more.

The convex-shaped portion formed by the central curving unit can be supported by a portion between the central curving unit and the first curving unit where the rigidity is higher, and the stability of the convex shape formed by the central curving unit can be improved.

In addition, a central groove or a slit extending in the longitudinal direction may be configured at a central part of the central curving unit. By providing the central groove or slit extending in the longitudinal direction at the central part of the central curving unit, a concave-shaped portion concaved at a non-skin contact surface side can be provided, and a liquid scattering effect in a central part in the widthwise direction of the absorber can be attained. For example, in at least one embodiment, in an absorber having a double-layered structure, a groove is provided at a central part of the upper layer of the absorber, and six central elastic members are arranged to be spaced by 5 mm, 10 mm, and 15 mm, respectively, from a centerline in the widthwise direction of the absorber without any elastic member being arranged on the centerline in the widthwise direction.

In at least one embodiment, a side edge (leg standing gather) including a side elastic member 90 is set at a position which is higher than a second side slit 47 configuring a second curving unit, namely, at a wearer's side.

Figure 9:
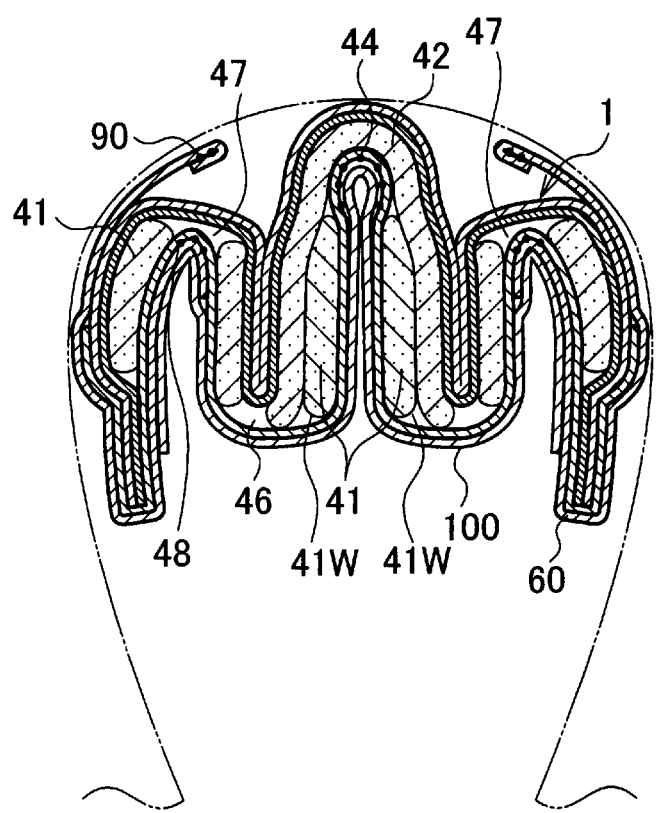
FIG. 9 is a cross section (when the wearer's legs are closed) schematically showing a state in which the disposable diaper 1 according to at least one embodiment is worn.

FIG. 9 is a cross section schematically showing a state in which a disposable diaper 1 is worn in a case the legs of a wearer are closed (taken along the line X1-X'1 of FIG. 2). It is to be noted that the virtual line in the figure shows a crotch portion and both leg portions of the wearer.

As shown in FIG. 9, when the wearer's legs are closed, the sectional shape of the disposable diaper 1 varies from the state shown in FIG. 8 to the state shown in FIG. 9. In a case where the wearer closes both legs, the absorber is folded at the central curving unit, the first curving unit, and the second curving unit, and is compactly arranged downward of the crotch portion in a state in which the convex-shaped and/or concave-shaped portions formed by these units come into intimate contact with each other.

At this time, the convex-shaped portion formed by the central curving unit that is formed of the central elastic member 44 and the central aperture 45 is positioned so as to abut against the crotch portion of the wearer. On the other hand, the concave-shaped portion formed by the first curving unit that is formed of the first side slit 46 is formed in a convex shape on a non-skin contact surface side, and does not abut against the wearer's excretion portion. Further, the convex-shaped portion formed by the second curving unit that is formed of the second side slit 47 is lower than the convex-shaped portion formed by the central curving unit, and is set at a lower position of the wearer's crotch portion.

Since the absorber comes into intimate contact with the wearer's crotch portion, even in a case where urine is discharged to such an extent that the urine flows along the wearer's skin, a leakage of bodily liquid can be prevented. In addition, in a folded state, the concave-shaped portion formed by the first curving unit is spaced from the skin of the wearer, and forms concavity extending in the longitudinal direction, thus making it possible to scatter bodily liquid to the outside in the longitudinal direction and making it possible to prevent a side leakage.

In addition, when the disposable diaper 1 is worn, a portion corresponding to a side edge elastic member 49 of the absorber 40 is lifted to the wearer's body side. A slit elastic member 48 is not provided between side edge elastic members 49 in the widthwise direction W. Therefore, the absorber 40 is formed in a curved shape along the buttocks part without being deformed in a convex shape by means of the slit elastic member 48 or the like.

Since the absorber is folded around the central aperture 45, the first side slit 46, and the second side slit that are formed in the absorber, the absorber 40 easily curves even in a case where the absorber 40 is swollen by absorbing a liquid in comparison with a case in which a portion of which thickness is small is formed at the absorber 40 to thereby obtain a convex-shaped portion. In addition, a sectional shape formed when the absorber 40 is deformed by wearing the disposable diaper 1 is in a tapered shape which is narrow from a non-skin contact surface side toward a skin contact surface side. Specifically, the sectional shape is formed in a tapered shape which is narrow from the lower region 40D, toward the upper region 40U, the wearer is unlikely to feel the discomfort of the disposable diaper getting stuck in the gap of the crotch portion of the wearer.

In addition, the convex-shaped portion which is formed by the central curving unit is configured by only the second layer 42, and is smaller in thickness than a portion at which the first layer 41 and the second layer 42 are laminated. That is, since the convex-shaped portion that is formed by the central curving unit is small in thickness, and is greater in height, this portion is easily inserted into a narrow gap of the crotch portion of the wearer, and easily comes into intimate contact with the excretion portion of the wearer. Therefore, for example, a urine discharge portion of the wearer and the absorber come into intimate contact with each other, making it possible to speedily absorb the discharged urine. In addition, at a portion which is proximal to the skin of the crotch portion of the wearer, the thickness of the absorber is small, and the absorber is folded so that the thickness is large at a portion which is distant from the skin, thus making it possible to ensure a fitting property without imparting the discomfort of the crotch portion of the wearer.

The absorber 40 has an extension region S51, thus making it possible to widely ensure an area of an absorber in a crotch region S3 which is positioned in the vicinity of an excretion portion of the wearer, and making it possible to enhance absorption performance and prevent the leakage in the crotch region S3. Even in a case where the area of the crotch region is increased, the absorber is folded by means of a plurality of curving units, thus making it possible to compactly dispose the absorber at the crotch of the wearer, and making it possible maintain a good comfort of the wearer when worn while ensuring absorption performance.

A method for manufacturing the thus configured absorbent article includes the steps of molding a first layer of an absorber, molding a second layer of the absorber, integrating the first layer and the second layer with each other, and conveying the absorber by means of a belt conveyor or the like, and then, bonding a sheet member such as a topsheet in a course of conveyance. It is to be noted that other steps are applicable in accordance with further embodiments.

In addition, in a case where apertures or a side slits are provided in both of the first layer and the second layer, there may occur a displacement when the first layer and the second layer are superimposed on each other. For example, if a displacement occurs in a widthwise direction, widths of a pair of side slits which are arranged at the left and right each become small, irregular deformation becomes possible, a transversely unbalanced absorber might be obtained, and absorptivity or the comfort when worn may be adversely affected. However, by providing apertures and/or side slits in either one of the first layer and the second layer, it is possible to prevent a displacement in side slit or the like.

Modification Embodiments

Figure 10:
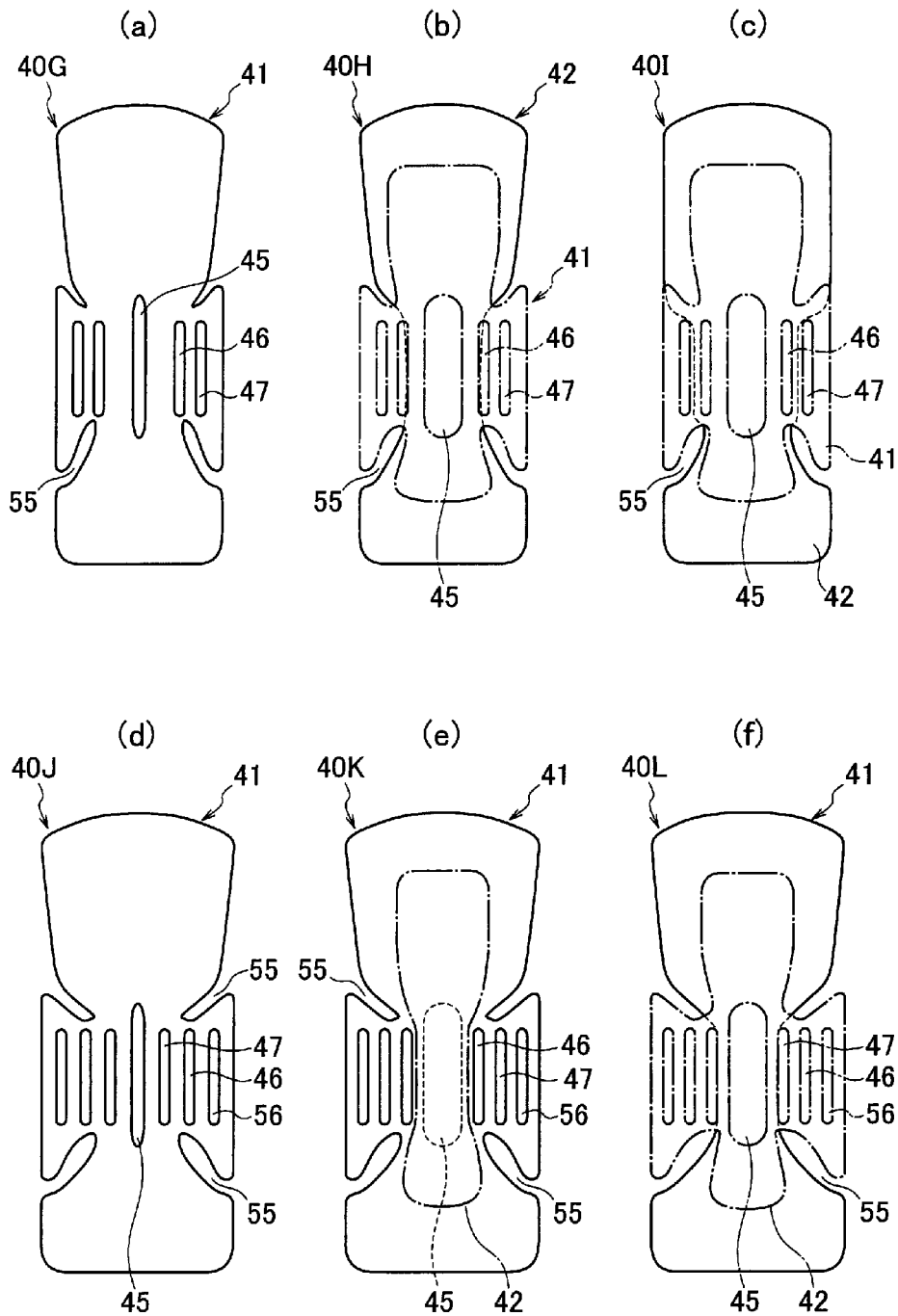
FIG. 10 is a plan view of an absorber of the disposable diaper 1, according to a modification embodiment.
Figure 11:
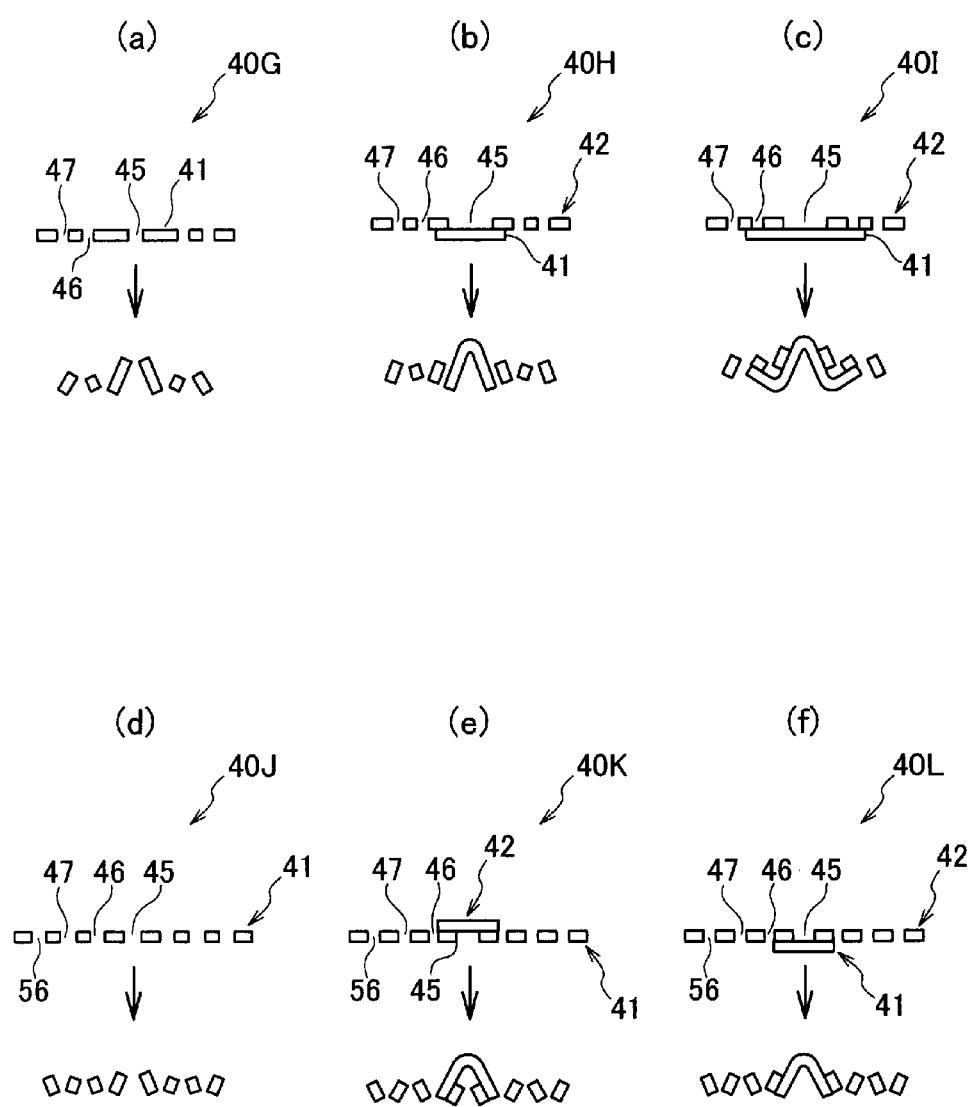
FIG. 11 is a sectional view of the absorber of the disposable diaper 1, according to the modification embodiment.

Next, the configuration of the absorbers 40G, 40H, 40I, 40J, 40K, and 40L of a disposable diaper according to a modification embodiment is explained with reference to drawings. Note that the same symbols are used to denote portions similar to those of the foregoing described embodiments, and the differences between the embodiments are mainly explained below. FIG. 10 is a plan view of the disposable diaper according to modification embodiments 1 to 6. FIG. 11 is a schematic cross section showing a state before deformation of the absorbers according to the modification embodiments. FIG. 11 shows a cross section in a narrow region S32 of the absorber.

The absorbers according to modification embodiments 1 and 4 are formed of only a first layer 41. The absorbers according to modification embodiments 2, 3, 5, and 6 are formed of a first layer 41 and a second layer 42.

The absorber 40G according to modification example 1, as shown in FIG. 10 (a), is formed of only a first layer 41, and in the first layer 41, a concave unit 55, a central aperture 45, a pair of first side slits 46 and a pair of second side slits 47 are formed. A width of a central aperture 45 is 12 mm, which is smaller than that of at least one embodiment described above with respect to FIGS. 1-9.

In the absorber 40H according to modification embodiment 2, as shown in FIG. 10 (b), the shapes of the first layer and the second layer are reversed from those of at least one embodiment described above with respect to FIGS. 1-9. That is, the first layer in which a side slit or a concave unit is formed is arranged at an upper side, and the second layer formed in a hourglass-shape in which no slit or the like is formed is arranged at a lower side.

In the absorber 40I according to modification embodiment 3, as shown in FIG. 10 (c), as is the case with the absorber according to modification embodiment 2, a central aperture or the like is formed in the second layer. An outside edge 41W in the widthwise direction of the first layer 41 is arranged in the vicinity of an inside edge in the widthwise direction of the second side slit 47 in a crotch region.

In the absorber 40J according to modification embodiment 4, as shown in FIG. 10 (d), a third side slit 56 is formed outboard of the second side slit 47 in the widthwise direction.

In the absorber 40K according to modification embodiment 5, as shown in FIG. 10 (e), an outside edge in the widthwise direction of the first layer is arranged in the vicinity of an inside edge in the widthwise direction of the first side slit 46. Further, a third side slit 56 is formed outboard of the second side slit in the widthwise direction.

In the absorber 40L according to modification embodiment 6, as shown in FIG. 10 (f), the shapes of the first layer and the second layer of the absorber are reversed from that of the absorber according to modification embodiment 5. Further, the third side slit is formed outboard of the second side slit in the widthwise direction.

As in the absorber according to modification embodiments 4 to 6, the third side slit is provided outboard of the second side slit in the widthwise direction, thereby making it possible to increase the number of times of folding of the absorber, and making it possible to dispose the absorber more compactly. In addition, it is possible to increase a width of the absorber in the crotch region, making it possible to increase an absorption capacity.

Further, a distance from a center in the widthwise direction of the central aperture 45 to an inside edge in the widthwise direction of the first side slit 46 is a, a distance from an outside edge in the widthwise direction of the first side slit 46 to an inside edge in the widthwise direction of the second side slit 47 is b, a distance from an outside edge in the widthwise direction of the second side slit 47 to an inside edge in the widthwise direction of the third side slit is c, and a distance from an outside edge in the widthwise direction of the third side slit 56 to an outside edge in the widthwise direction of the absorber is d. In at least one embodiment, a>b, a>c, and a>d. Additionally in at least one embodiment, d<b, d=b, d<c, and d=c.

According to the thus structured absorber 40, it is possible to reduce a sectional width of the absorber that is positioned in the upper region 40U increase a sectional width of the lower region 40D, and easily fit to the wearer's crotch portion.

Other Embodiments

As described above, although several embodiments of the present invention are disclosed, the description and drawings forming part of this disclosure are not intended to limit the present invention. From this disclosure, a variety of substitutive embodiments, examples, and operational techniques would become apparent to one ordinarily skilled in the art.

For example, while, in the foregoing embodiments, a pants-type disposable diaper was described by way of example, the present invention is not limited thereto, and may be applied to an open-type disposable diaper, an incontinence pad, and a sanitary napkin or the like.

While, in the foregoing embodiment, an absorber was configured to curve by employing a slit, an elastic member, or a boundary portion of which rigidity varies, an absorber may be configured to curve by reducing the thickness of the absorber or by applying emboss processing to the absorber.

In addition, while the absorbent article according to at least one embodiment includes a side edge elastic member 49, the side edge elastic member 49 is omitted in some embodiments. Further, while a leakage-proof wall has an erected portion (side elastic member 90) in order to prevent a side leakage from the crotch, the side elastic member 90 is omitted in some embodiments.

While, in at least one embodiment, the absorber 40 is a double-layered structure of the first layer 41 and the second layer 42, the absorber is formed of only one layer, or alternatively, of three or more layers in some embodiments.

Thus, it is needless to say that the present invention includes various embodiments not specifically described herein. Therefore, the technical scope of the present invention is defined only by the inventive specific matter according to the scope of the claims appropriate from the above description.

This application claims the benefit of Japanese Application No. 2011-147784 the entire disclosure of which is incorporated by reference herein.

The invention claimed is:

1. A disposable wearing article, comprising an absorber having a longitudinal direction extending to a body foreside and a body backside of a wearer, a widthwise direction perpendicular to the longitudinal direction, an inner direction for facing the wearer and an outer direction opposite the inner direction,
   the absorber having a crotch region that is adapted to be in contact with a crotch of the wearer, a front waistline region arranged anteriorly of the crotch region, and a back waistline region arranged posteriorly of the crotch region, wherein
   a central curving unit that allows the absorber to curve in a convex shape in the inner direction is formed at a center in the widthwise direction of the crotch region,
   a first curving unit that allows the absorber to curve in a convex shape in the outer direction is formed in the crotch region and outboard of the central curving unit in the widthwise direction,
   a second curving unit that allows the absorber to curve in a convex shape in the inner direction is formed in the crotch region and outboard of the first curving unit in the widthwise direction,
   a concave unit is formed in the absorber to be concaved inwardly in the widthwise direction, and at an outside in the longitudinal direction relative to the first curving unit, and
   the second curving unit is arranged outboard of an inside edge in the widthwise direction of the concave unit in the widthwise direction.

2. The disposable wearing article according to claim 1, wherein the concave unit includes a first concave portion arranged anteriorly of the first curving unit and a second concave portion arranged posteriorly of the first curving unit.

3. The disposable wearing article according to claim 2, wherein
   the absorber has a region which is positioned between the first concave portion and the second concave portion,
   the region is formed in a shape which extends outwardly in the longitudinal direction and outwardly in the widthwise direction.

4. The disposable wearing article according to claim 1, wherein the absorber includes:
   a first layer positioned at a non-skin contact surface side; and
   a second layer overlapping the first layer and positioned at a skin contact surface side, and wherein
   the central curving unit, the first curving unit, and the second curving unit are formed in either one of the first layer and the second layer.

5. The disposable wearing article according to claim 1, wherein a distance in the widthwise direction between the central curving unit and the first curving unit is longer than a distance in the widthwise direction between the first curving unit and the second curving unit.

6. The disposable wearing article according to claim 1, wherein a top face of the absorber is adapted to be formed in a convex shape in the inner direction by the central curving unit, and is configured to be in contact with a crotch of the wearer.

7. The disposable wearing article according to claim 1, wherein each of the central curving unit, the first curving unit, and the second curving unit comprises a slit formed at the absorber along the longitudinal direction or an elastic member positioned along the longitudinal direction.

* * * * *